United States Patent [19]
Schneider et al.

[11] Patent Number: 5,358,613
[45] Date of Patent: Oct. 25, 1994

[54] METHOD AND APPARATUS FOR INJECTING LIQUID INTO A CAPILLARY TUBE

[75] Inventors: Werner Schneider, Ettlingen; Klaus Witt, Keltern, both of Fed. Rep. of Germany

[73] Assignee: Hewlett-Packard Company, Palo Alto, Calif.

[21] Appl. No.: 174,286

[22] Filed: Dec. 27, 1993

[30] Foreign Application Priority Data

Jan. 21, 1993 [EP] European Pat. Off. ........ 93100847.8

[51] Int. Cl.⁵ .............................................. B01D 57/02
[52] U.S. Cl. ............................. 204/180.1; 204/299 R
[58] Field of Search .............. 204/180.1, 182.8, 299 R

[56] References Cited

FOREIGN PATENT DOCUMENTS

0339781A3 11/1989 European Pat. Off. .
0395796A1 11/1990 European Pat. Off. .
0475533A3 3/1992 European Pat. Off. .
0479137A2 4/1992 European Pat. Off. .

OTHER PUBLICATIONS

"Characterization and Automation of Sample Introduction Methods For Capillary Zone Electrophoresis", D. J. Rose, et al., vol. 60, No. 7, Apr. 1988, pp. 642–648.
European Search Report, 3 pages, Jul. 2, 1993.

*Primary Examiner*—John Niebling
*Assistant Examiner*—Edna Wong

[57] ABSTRACT

In a method and a corresponding apparatus for injecting liquid from a vial into a capillary tube, in particular in capillary electrophoresis, a source of overpressure and a source of underpressure are connectable to the vial for applying overpressure or underpressure in the space above the liquid. During an injection, the pressure is continuously varied in a controlled way by corresponding control of the pressure sources, for example by controlling associated valves. The pressure is first gradually increased and then gradually decreased. The actual pressure variation during an injection is measured by a pressure sensor and used by a controller to control the durations of the time intervals during which overpressure or underpressure are applied such that a desired amount of liquid is introduced into the capillary.

11 Claims, 4 Drawing Sheets

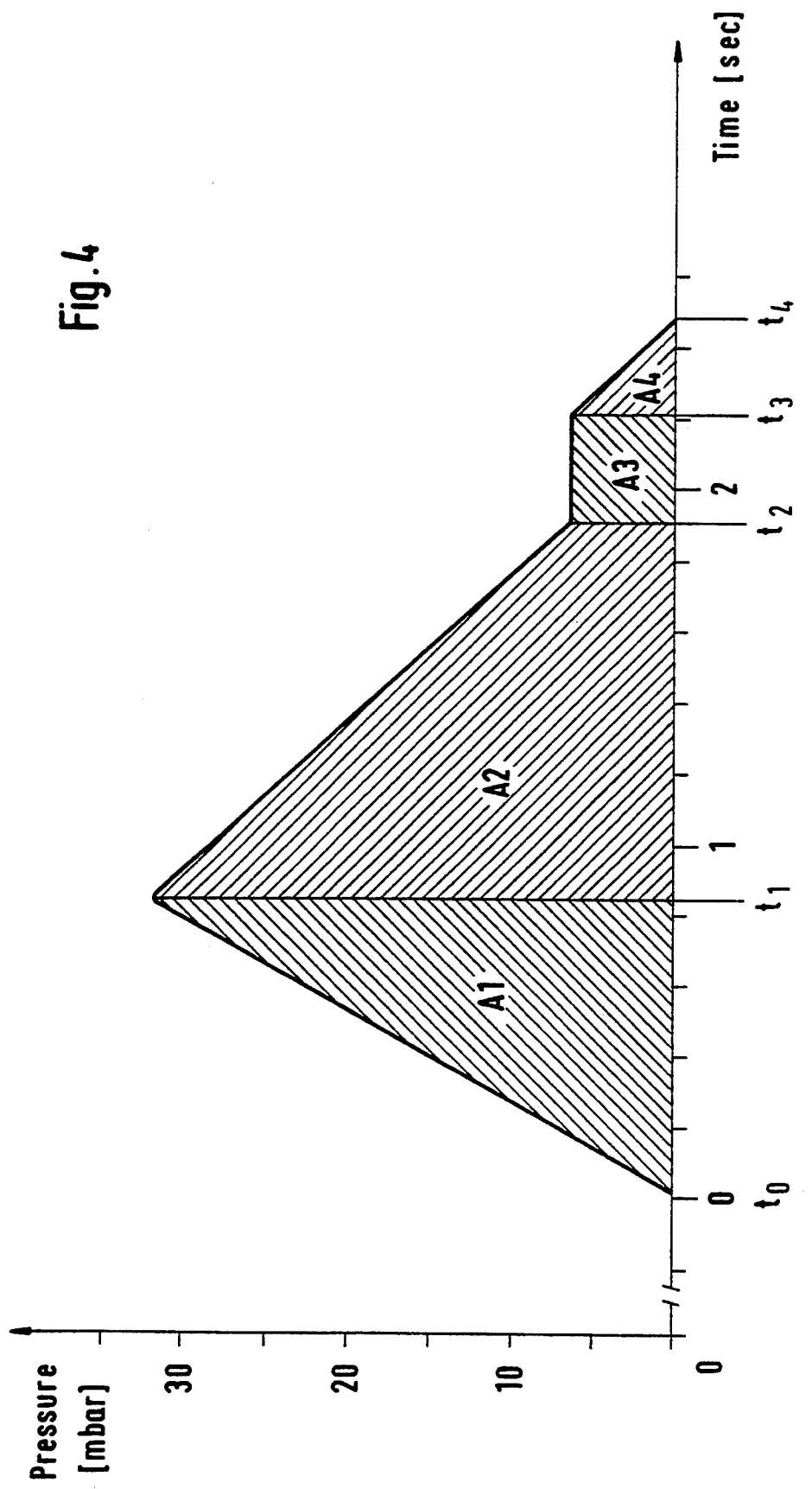

METHOD AND APPARATUS FOR INJECTING LIQUID INTO A CAPILLARY TUBE

The invention relates to a method and an apparatus for injecting liquid into a capillary tube. Such a method is used, for example, in capillary electrophoresis for introducing samples into the separation capillary.

BACKGROUND OF THE INVENTION

Capillary electrophoresis is a separation method employed in analytical chemistry which utilizes the differences in electrophoretic mobility of the sample substances to be separated. Capillary electrophoresis is used, for example, for separating different biological molecules, such as proteins or peptides. The separation process is performed in a capillary tube which is typically open on both ends and to which an electric field is typically applied which causes electrophoretic separation of different sample substances within the capillary tube. The electric field is applied by means of electrodes which are arranged at the ends of the capillary, respectively, and which are connected to a high voltage power supply. The capillary is filled with an electrically conductive electrolyte so that an electric field can build up within the capillary. The two ends of the capillary are immersed in vials containing the electrolyte, respectively.

When new sample substances are to be introduced into the capillary for subsequent separation, the vial containing the electrolyte is removed from one end of the capillary, a vial containing the sample is positioned at this place so that the end of the capillary is immersed in the sample liquid. Thereafter, the sample is injected into the capillary. In the state of the art, basically two different methods for sample injection have been developed: the first method is based on electromigration, and the second method is based on pressure differences between the first and the second end of the capillary tube.

According to the injection method based on electromigration, an end of the capillary and an electrode are placed into the sample and a voltage is briefly applied which causes an amount of sample liquid to electromigrate into the capillary under the action of the applied electric field. A disadvantage of this method is that the injection already causes a preseparation of the sample components due to different ionic strength and resulting electrophoretic mobility of the sample substances. A further disadvantage is that electrochemical by-products may be created which may contaminate sensitive samples.

According to the injection method based on pressure differences, the sample is forced into the capillary by an outer pressure difference which may be created either by positioning the outlet end of the capillary at a different level than the inlet end, or by applying overpressure at the inlet end or underpressure at the outlet end of the capillary. A method of the first type wherein inlet and outlet ends of the capillary can be positioned at different levels for the injection step is known from the article D. J. Rose and J. W. Jorgenson, "Characterization and Automation of Sample Introduction Methods for Capillary Zone Electrophoresis" Analytical Chemistry 60 (1988), pages 642-648. This approach has some disadvantages. First, an apparatus using this injection method requires a comparatively large space since the capillary has to be moved over a certain distance. Second, the protection of the user against high voltage and the removal of heat from the capillary generated during electrophoresis require considerable expenditure due to the mobility of the capillary.

According to a further known injection method, sub-atmospheric pressure is used to introduce the sample. For this purpose, the outlet end of the capillary where the detector is located comprises corresponding arrangements for generating sub-atmospheric pressure. This has the disadvantage that it is difficult or impossible to couple further analytical instruments and/or detectors to the outlet of the electrophoresis apparatus. Furthermore, the known method uses a comparatively large underpressure for the injection which leads to very small injection times. As a consequence of these short injection times, the accuracy of the electrophoretic separation is impaired. In order to explain this, some general remarks on sample injection will now be made.

The purpose of an injection is to introduce a quantitatively defined volume of sample into the separation capillary. The relationship between the flow in a tube and the pressure difference is described by the law of Hagen-Poisseuille: In a capillary tube of a given length and internal diameter, the flow is proportional to the pressure difference and inversely proportional to the viscosity of the liquid. For a sufficiently short time, for example a couple of seconds, the viscosity can be considered constant so that the flow is proportional to the pressure acting on one end of the capillary if the pressure at the other end is constant, for example ambient pressure. From the above it follows that in case of a constant pressure the injected volume is proportional to the time during which the pressure acts. In case of a variable pressure, the injected volume is proportional to the time integral of the pressure curve. For a given pressure, the injection time becomes smaller if the sample volume to be introduced becomes smaller. For very small injection times, the switching and delay times of the hydraulic and pneumatic components become relevant so that the quantitative accuracy of the electrophoretic separation is impaired. This explains the disadvantages of the above mentioned prior art method. A further limitation of the pressure injection methods arises at low pressures if the velocity of the liquid which is caused by the application of the pressure, is in the range of the diffusion velocities of the sample components. If this is the case, the selectivity of the electrophoretic separation is impaired.

A further prior art injection device is disclosed in EP-A-0 475 533. This known device does not use a permanent pressure source but a kind of piston pump which is brought in relationship with the vial containing the sample liquid. When pushing the piston inwardly, the gas pressure in the sample vial increases so that sample is forced into the capillary. In order to achieve a high injection accuracy with this device, it is important that all components are well sealed against the environment and that all seals are durable and reliable. Otherwise, the injected volumes would be dependent on the ambient pressure so that fluctuations of the ambient pressure would lead to measuring errors.

From EP-A-0 339 781, an injector for a capillary electrophoresis apparatus is known wherein overpressure is applied to the liquid to be injected at the end of the capillary distant from the detector. The pressure applied is substantially constant during the injection. At the beginning of the injection, the pressure value quickly jumps to the desired constant value. The pressure is measured by a pressure sensor and integrated with respect to time to derive the flow rate for determining the volume introduced into the capillary. By comparison of the measured injection volume with the desired volume entered by a user, control signals for controlling the valves of the injector are produced. Such a control signal causes the switching off of valves at the end of an injection period. In response thereto, the pressure drops again to ambient pressure, but this decrease occurs passively, without active pressure control so that it may come to fluctuations from one injection to another. Such fluctuations may be caused, for example, by changes in the ambient pressure or by temperature changes. Furthermore, the specifications for the components of the injector might be different for different devices which also leads to unwanted deviations. For small injected volumes, the accuracy may be impaired. Furthermore, the abrupt application of the pressure at the beginning of an injection may cause sloshing around and splashing of the sample liquid which may lead to sample loss and/or to a higher evaporation rate of the carrier liquid and thus to a change in the sample concentration.

SUMMARY OF THE INVENTION

It is thus an object of the present invention to provide a method for injecting liquid into a capillary tube and a corresponding apparatus for performing such a method which allows to inject smaller quantities of liquid into the capillary tube with the same or an improved repetition accuracy than in the prior art.

It is a further object to provide an injector for a capillary electrophoresis apparatus which allows easy coupling of additional instruments, such as additional detectors or separation devices, to the outlet end of the capillary.

A further object is to provide to the user of an electrophoresis apparatus more flexibility in injecting liquid in the capillary and in manipulations of the liquid introduced into the capillary.

According to the present invention, these objects are solved for a method by the features of claim 1 and for an apparatus by the features of claim 6. In accordance with the invention, the liquid is introduced into the capillary by application of a fluid pressure on the liquid whereby this pressure gradually increases in a controlled way during a first time interval up to a certain pressure value and thereafter decreases from this pressure value in a controlled way during a second time interval. Unlike in prior art injectors, there is no sudden increase and reduction of the fluid pressure, but pressure build-up and pressure reduction are actively performed in a controlled way so that it cannot come to uncontrolled processes which would impair the accuracy of the injection. The method of the invention can be realized by providing a controllable source of overpressure and a controllable source of underpressure which are controlled such that the described smooth pressure variation is accomplished.

In a preferred embodiment of the invention, the actual fluid pressure during an injection is measured and from this value the amount of liquid injected is derived. Furthermore, an automatic control is provided which regulates the amount of liquid actually injected to a desired nominal value which has been entered by a user. This is accomplished in the following manner: After reduction of the fluid pressure to a certain value, a variable time interval follows during which the fluid pressure is kept at a known value. The duration of this time interval is adjusted by the automatic control such that the desired nominal value is achieved. In that way, very precise injections are possible, even if the components of the apparatus are not absolutely leakproof or if these components have manufacturing tolerances or change their specifications in the course of time. Furthermore, fluctuations in temperature and ambient pressure can be compensated for. In particular, the invention allows the use of commercially available cost-saving components and still ensures high accuracy.

The invention has the following further advantages:

Due to the continuous pressure variation, disturbing influences on the sample in an electrophoresis apparatus are avoided. Since the outlet end of the capillary does not comprise any components, it is possible to couple further instruments to the capillary electrophoresis apparatus. Since the valves in an apparatus of the invention are activated either in a state of zero pressure or during an action within the controlled time frame, electrical and, more important, mechanical switching times of the valves and the circuitry have no disadvantageous impact. Furthermore, there is virtually no limit in the duration of a pressure exposure since a permanently running pump can be used as the source for overpressure and underpressure, in contrast to the syringe device according to EP-A-0 475 533.

In an embodiment of the invention, the source of overpressure and the source of underpressure are realized by a single pump which is connected via controllable valves to a working volume. If air flows into the working volume or is drawn off the working volume, the required smooth increase or decrease of the pressure acting on the liquid to be injected is achieved. This embodiment constitutes a simple and reliable design for the source of overpressure and the source of underpressure.

BRIEF DESCRIPTION OF THE DRAWINGS

Subsequently, an embodiment of the invention will be explained in detail with reference to the drawings.

FIG. 4 is a diagram illustrating the variation of the pressure for the injection as a function of time, in accordance with a practical example of the invention.

DETAILED DESCRIPTION OF THE INVENTION

Figure 1:
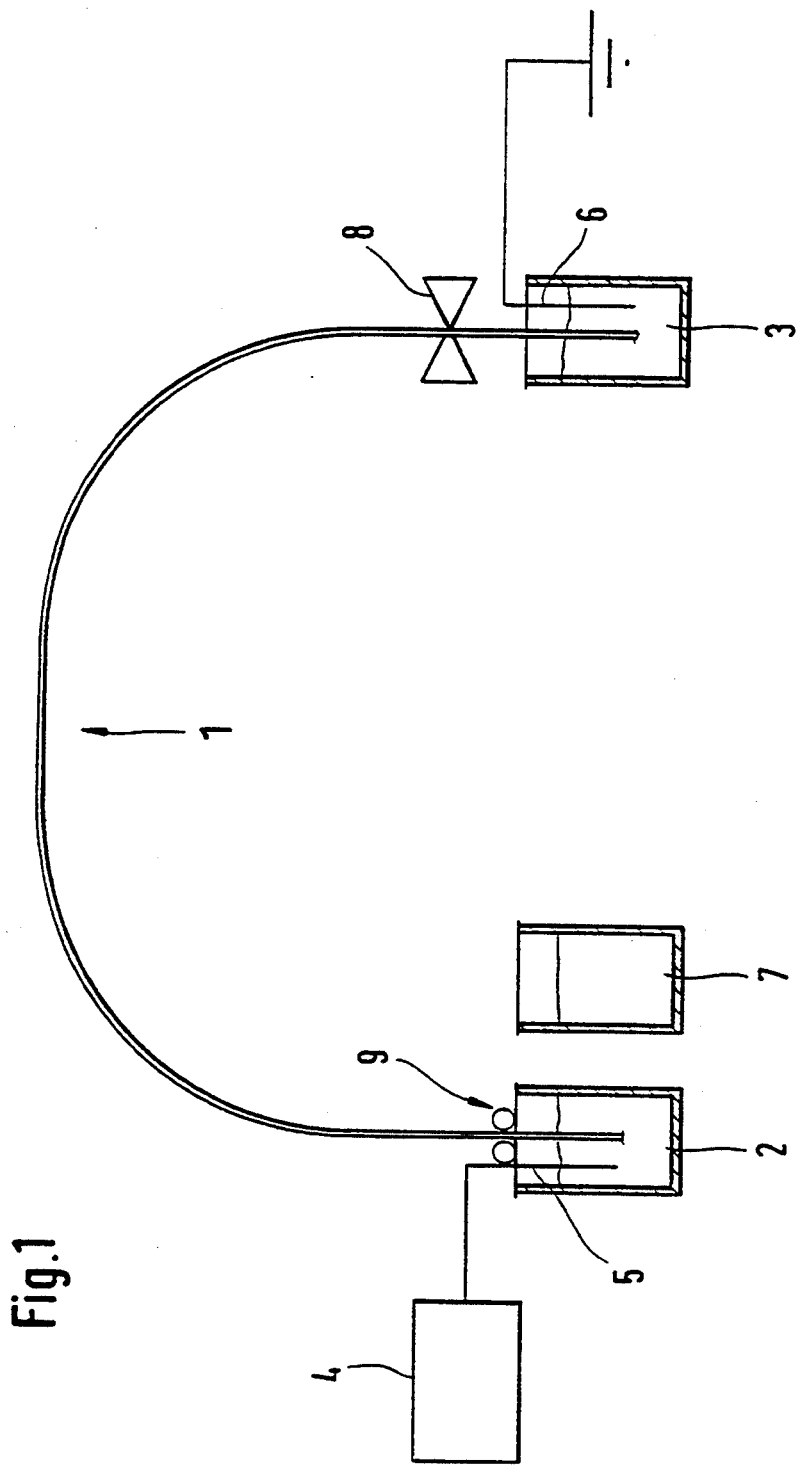
FIG. 1 is a schematic diagram illustrating the basic components of a capillary electrophoresis apparatus FIG. 2 schematically shows an embodiment of a liquid injector according to the invention.

FIG. 1 schematically depicts the components of a capillary electrophoresis apparatus. The separation column is immersed with its inlet in a first vial 2 containing electrolyte and with its outlet end in a second vial 3 which also contains electrolyte. An electric field is applied along the capillary 1 by a high-voltage power supply 4 via an electrode 5 at the inlet end of the capillary 1. An electrode 6 at the outlet end of the capillary 1 is connected to ground potential. A sample vial 7 contains the sample substances to be separated electrophoretically. For introducing the sample substances into the capillary 1, the vial 2 is replaced by the sample vial 7 and a plug of sample liquid is injected into the capillary 1 by generating pressure differences relative to ambient pressure. For maintaining such a pressure difference, a sealing arrangement 9 is provided. Details of the sealing arrangement and the injection process will be explained below. The sample substances separated in the capillary are detected by a detector 8 which is arranged at the outlet end of the capillary 1. The detector 8 can be, for example, a UV absorbance detector. The detector 8 is connected to a processing circuit (not shown) which produces signals indicative of the substances passing the detector. The capillary 1 is typically made of fused silica.

Figure 2:
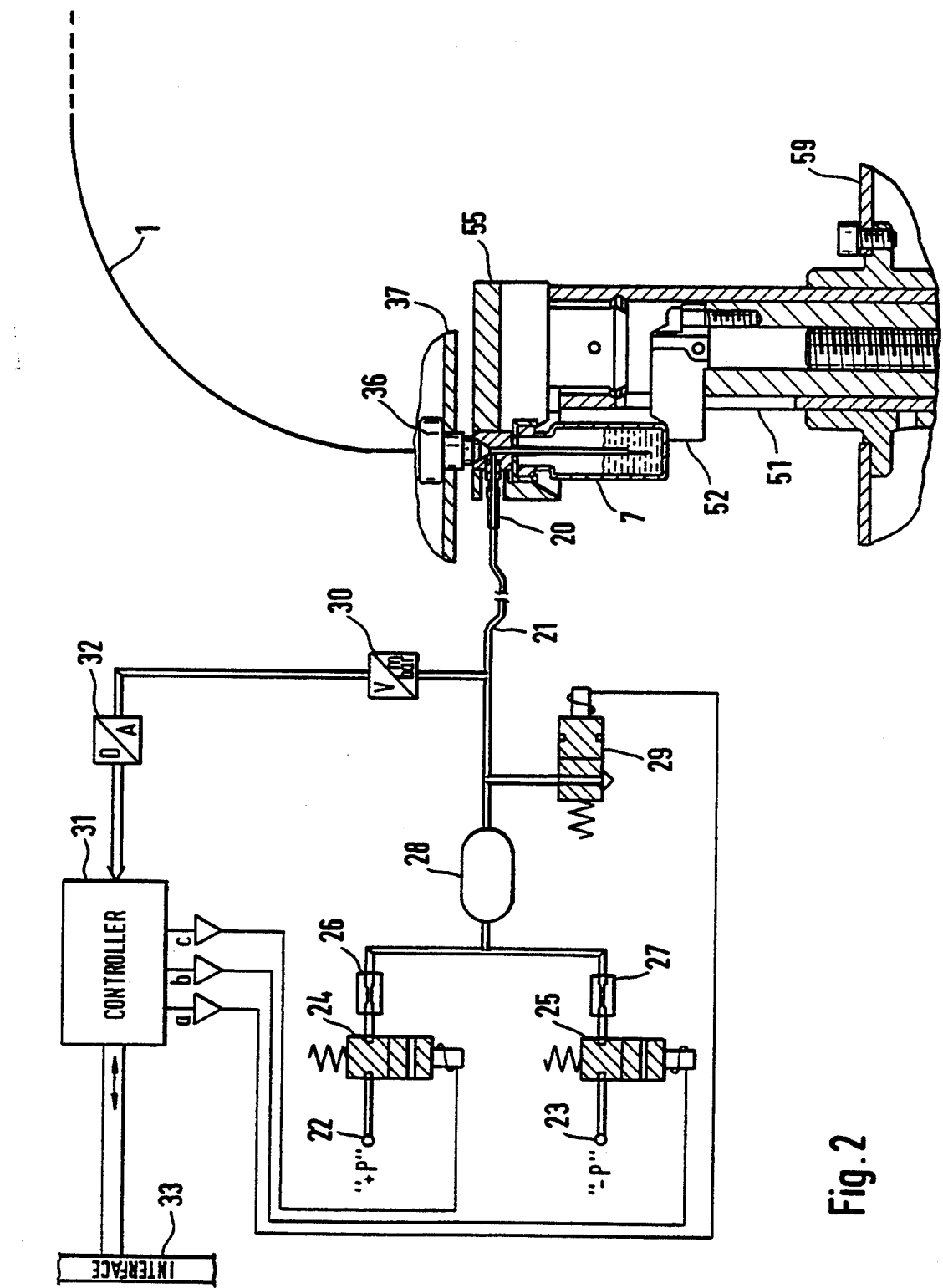

FIG. 2 schematically shows an embodiment of an apparatus according to the invention. The capillary 1 is immersed in the sample liquid contained in the vial 7. The capillary 1 is typically arranged in a capillary cassette in which it may be wound in the form of a coil. For the sake of simplicity, the cassette is not shown. A high voltage insulation plate 37 is provided to which a capillary seal and electrode arrangement 36 is fastened. Details of the arrangement 36 will be explained below with reference to FIG. 3. The vial 7 is held by a lifting device 51, in particular by a lifting finger 52 which can be moved vertically up and down. In that way, the liquid inside the vial 7 can be brought into contact with the end of the capillary 1 for injecting liquid into the capillary and it can be lowered when the injection has been completed. The lifting device 51 is fastened to a platform 59. A capillary electrophoresis apparatus using the present invention may comprise an additional lifting device at the second end (not shown) of the capillary 1 for lifting an electrolyte vial such that the capillary end dips into the electrolyte. Such an additional lifting device is also fastened to the platform 59 and, like the lifting device 51, arranged close to a sample tray containing a plurality of sample and electrolyte vials such that a lifting finger of the lifting device, for example lifting finger 52, can raise the vial out of the tray towards an end of the capillary. An electrophoresis apparatus comprising several lifting devices of the type mentioned is disclosed in applicant's European patent application No. 92113245.2 entitled "Apparatus for handling liquid vials in an analytical device".

The introduction of liquid from the vial 7 into the capillary 1 is accomplished by means of a pressure system which will now be described. It is understood that during an injection the second end (not shown) of the capillary is also immersed in a liquid. The pressure system is coupled to the vial 7 via a pipe 20 and a tube 21 connected to the pipe. Via the tube 21 and the pipe 20, a pressure above ambient pressure or below ambient pressure can be applied in the vial 7. A source of overpressure 22 and a source of underpressure 23 are provided which can be switched in fluid communication with the tube 21. The source of overpressure 22 is connected via a valve 24 and a pneumatic restrictor 26 to a working volume 28. The source of underpressure 23 is connected via a valve 25 and a pneumatic restrictor 27 to the working volume 28. The tube 21 is connected to the exit of the working volume 28. A valve 29 provides for a connection to the atmosphere for avoiding pressure disturbances during handling of the sample vials. During an injection of liquid into the capillary 1, the valve 29 is closed. A pressure sensor 30 measures the pressure in the tube 21.

The opening and closing of the valves 24, 25, and 29 is controlled by a controller 31 which emits control signals on lines a,b,c, respectively. The control signals on lines a,b,c are amplified in a suitable manner by driver circuits before being supplied to the valves. The controller 31 typically comprises a microprocessor. Also shown in FIG. 2 is an interface 33 which serves for the connection to remaining circuitry of the electrophoresis apparatus, for example control circuits for vial handling. The output signal of the pressure sensor 30 is converted to digital signals by an A/D converter and supplied to the controller 31. The controller emits the control signals on lines a,b,c in response to the input from the A/D converter 32 and in response to the desired injection parameters entered by a user. The way how these control signals are derived will be explained below in connection with FIG. 4.

According to an embodiment of the invention, a single pump, for example a membrane pump, can be used for providing a source of overpressure 22 and a source of underpressure 23. By suitable switching over between two operating modes, such a pump generates a pressure above ambient pressure in a first mode, and a pressure below ambient pressure in a second mode. In an embodiment of the invention, in particular in an electrophoresis apparatus, the pump is not only used for the injection, but also for performing additional functions of the apparatus, such as rinsing, replenishing, etc. The pump is permanently running after the electrophoresis apparatus has been switched on and provides for a permanent supply of overpressure +P and underpressure −P which can be tapped at various locations in the apparatus. In a practical embodiment of the invention, the high pressure source provides a pressure of about 1000 mbar (above ambient pressure). The compressed air enters the restrictor 26 which produces at its output an air flow at an order of magnitude of 1 ml/s. This air flow is directed into the working volume 28 and gradually fills this space with air. As a consequence thereof, the pressure at the outlet of the working volume, i.e., in the tube 21 and therefore in the vial 7, increases uniformly. This pressure increase is illustrated in the pressure/time diagram of FIG. 4 between the times t0 and t1. When pressure is applied to the vial 7 in the manner just described, the valves 29 and 25 are closed and the working volume 28, the air space in the vial 7 and the volumes in the air conducting tubes of the pressure system form a closed system. The working volume 28 typically occupies 90% of this closed system. The application of an underpressure is accomplished in an analogous manner by connecting the tube 21 to the source of underpressure 23, with the valve 25 being opened and the valves 24 and 29 being closed.

It is understood that the pressure system shown in FIG. 2 can be realized in a plurality of ways. In an embodiment of the invention, the working space 28 corresponds to a cavity milled out inside a metal block, the valves 24, 25, and 29 are arranged on the side faces of this metal block, and the connecting tubes between the valves and the working volume as well as the restrictors 26 and 27 are milled in the metal block. In that way, a space saving, compact arrangement of the mentioned components is achieved.

Figure 3:
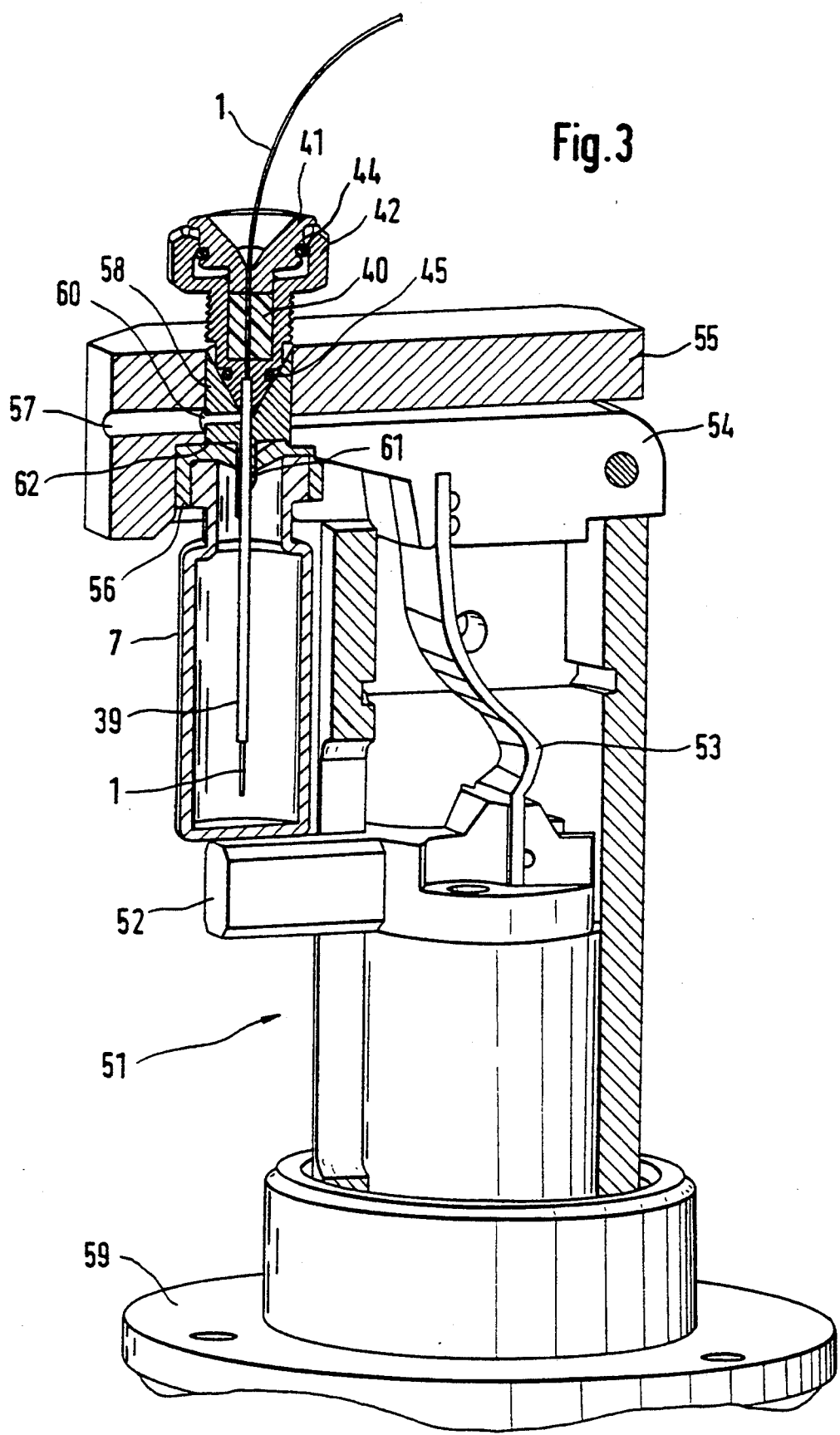
FIG. 3 is a detailed view, partially in cross section, of the vial lifting device shown in FIG. 2 and of the sealing arrangement associated with the lifting device.

Reference is now made to FIG. 3 which is a detailed view of the vial lifting device 51 shown in FIG. 2 and of the sealing arrangement 36 associated with the lifting device. The vial 7 is held in place by the lifting finger 52. The capillary 1 is arranged inside the vial 7. For the sake of clarity, the liquid in the vial into which the capillary dips, has not been shown. The capillary 1 is surrounded by an electrically conductive tube 39 which serves as an electrode for performing electrophoresis. The sealing arrangement 36 comprises a housing 42 made of an electrically conductive material. The housing 42 has a threaded portion at the outside which can be screwed into the insulation plate 37 (see FIG. 2). In FIG. 3, the insulation plate has not been drawn in order to keep the drawing simpler. The electrode tube 39 is pressed into the housing 42. A funnel shaped part 41 is held in the housing 42 by means of an O-ring 44. A second O-ring 45 is arranged at the lower part of the housing 42. An elastomeric seal 40 is arranged inside the housing 42. The seal 40 comprises a passage for the capillary 1.

When introducing the capillary 1, the funnel 41 catches the end of the capillary and guides it through the seal 40 and the electrode tube 39. The capillary is typically arranged in a cassette from which the two ends of the capillary protrude. When the cassette has been inserted in the electrophoresis apparatus, bottom of the cassette presses against the funnel 41 which in turn deforms the seal 40 so that it contacts the capillary 1 and the housing 42 and forms a tight seal.

A funnel shaped member 58 is inserted in the head portion 55 of the lifting device 51. The member 58 can accommodate the corresponding cone shaped lower part of the housing 42. The head portion has a recess into which the top of the vial 7 fits. The vial 7 is closed with a septum 56 which has been pierced by a punching needle 61 which protrudes downwards from the member 58. The member 58 also comprises an annular cutting edge 62 surrounding the punching needle 62. The cutting edge 62 cuts into the septum 56 when the vial 7 is pressed against the head portion 55 and thus provides for a sealing of the member 58 against the vial 7. When the vial 7 is to be positioned back in a vial tray, the lifting device 51 and the finger 52 have to be lowered. In order to ensure that the vial is removed from the punching needle when it is lowered, a rocking lever 54 and an actuation belt 53 are provided. When the finger 52 has been moved sufficiently far downwards, the actuation belt 53 is tightened, causing a tilting of the rocking lever 54 whereby the vial 7 is stripped off the punching needle 61.

The head portion 55 of the lifting device 51 comprises an inlet channel 57 to which the pipe 20 (only shown in FIG. 2) is connected. The application of pressure, either above or below atmospheric pressure, thus occurs through the channel 57 which in turn is connected to a channel 60 in the member 58 which is in fluid communication with the vial 7 through the interior of the punching needle 61. The escaping of the pressure applied to the interior of the vial is prevented by various seals: First, the bottom of the member 58 has the mentioned cutting edge 62 which cuts into the septum 56 and seals there. Second, an O-ring 45 is arranged in a groove of the housing 42 in order to prevent leaking through the funnel of the member 58. Finally, the seal 40 provides a seal around the capillary 1.

As mentioned above, the present invention is preferably used in a capillary electrophoresis apparatus. In this case, the sample tray for receiving sample and electrolyte vials is preferably of the type as described in applicant's above mentioned European patent application No. 92113245.2 and the design of the lifting station and of the capillary cassette is preferably of the type as described in applicant's European patent application No. 92113244.5 entitled "Apparatus for performing capillary electrophoresis".

In the following, a typical injection of liquid from the vial 7 into the capillary 1 will be described in detail with reference to FIG. 4. FIG. 4 is a diagram illustrating the variation of the pressure in the vial 7 as a function of time. The shaded area under the pressure curve corresponds to the integral of the pressure over time and is a measure of the amount of liquid injected into the capillary 1. In the example shown in FIG. 4, the shaded area is approximately 40 mbar s (millibarseconds). The value of pressure times duration of the injection (i.e., 40 mbars in the present example) can be selected by a user. The value entered by the user is provided to the controller 31 depicted in FIG. 2 via the interface 33. From this value, the controller derives the pressure curve for the injection in a manner to be described below. As shown in FIG. 4, the beginning of the injection is at the time t0, and the end of the injection is at time t4. The value 0 on the pressure axis corresponds to ambient pressure.

Before the injection starts, the valve 29 is activated by the controller 31 so that the pressure system as shown in FIG. 2 is sealed off the environment. Now, the working volume 28, the air space in the vial 7 and the volumes in the connecting tubes of the pressure system form a closed system. In the next step, starting at the time t0, the valve 24 is opened so that air slowly flows from the restrictor 26 to the working space 28 causing a uniform pressure increase up to the time t1. In the embodiment of the invention shown in FIG. 2, the slope of the pressure increase between t0 and t1 is substantially determined by the dimensions of the used components, such as the pressure value $+P$ and the dimensioning of the restrictor 26 and the working space 28. In the example shown, the time t1 is such that the area A1 under the pressure curve between t0 and t1 amounts to approximately 35% of the nominal value entered by the user, i.e., the desired product of time and pressure. At the time t1, the valve 24 is closed and the valve 25 is opened at the same time. As a consequence thereof, air is drawn off the closed system by the source of underpressure 23 so that the pressure decreases. This pressure decrease is shown in FIG. 4 between the time t1 and the time t2. It is important to note that the pressure build-up between t0 and t1 as well as the pressure reduction between t1 and t2 are performed actively in a controlled manner. Unlike in prior art devices wherein the pressure is abruptly applied or relieved, there are no uncontrolled processes which would lead to inaccuracies.

The pressure is reduced until a value of about 6 to 7 mbar is reached. This occurs at time t2. The area below the pressure curve between the times t1 and t2 is labelled with "A2". At the time t2, the valve 25 is closed so that the closed system is in a passive state. The pressure will then remain nearly constant up to the time t3. The pressure may slightly drop between t2 and t3 if there are leakages in the system. The area between t2 and t3 is labelled "A3". At the time t3, the valve 25 is activated again and the remaining pressure is actively reduced to zero. The corresponding area is A4. At the time t4, the initial pressure at the time t0 is reached again, all valves are switched off, and the injection cycle is finished.

The duration of the time interval between t2 and t3 is determined by the controller 31 using a control algorithm which works as follows:

As mentioned above, the area under the pressure curve, i.e., the sum $S = A1 + A2 + A3 + A4$, corresponds to the amount of liquid injected into the capillary. The purpose of the control algorithm is to control the time interval t2-t3 such that this sum equals the desired nominal value entered by the user. Since the pressure is permanently measured by the pressure sensor 30, the value A1+A2 is known at the time t2. Consequently, it is also known which value the sum A3+A4 must have in order to achieve the nominal value. Since the area A4 is known in advance before the time t4 is actually reached, the control algorithm is able to calculate the value of A3 which is necessary so that the total sum S has the nominal value. The value A4 can be calculated in advance because it depends on the pressure which is nearly constant and known through the measurement with the pressure sensor, and because the slope of the pressure curve between t3 and t4 is substantially equal to the slope of the pressure curve immediately before the time t2. The time t3 can thus be precisely determined during an ongoing injection process. According to a practical example, the components of the apparatus of the invention are dimensioned such that at the end of the main injection phase at the time t2, the sum A1+A2 is about 90-95% of the nominal value (A1+A2+A3+A4).

With the above described pressure variation, a precise injection even of very small sample quantities is possible. Since the pressure is increased and decreased in a controlled continuous manner, disturbing influences on the sample are avoided. Since the magnitude of the area A3 is controlled in response to the actually measured parameters during injection, it is possible to compensate for tolerances and variances of the components of the injection apparatus. It is thus possible to achieve high accuracy of the injection even when using commercially available, low-cost components. Furthermore, due to the active building up of the pressure, any (passive) build-up variances at the switching times of the pressure curve are avoided.

According to a further development of the invention, the control algorithm for determining the pressure variation during injection can still be further refined. The purpose of such a refinement is to avoid that the time interval t2-t3 becomes too long. If this time interval were too long, the total time for an injection would be so long that diffusion of the sample components would lead to a deterioration of the electrophoretic separation of the sample components. If it turns out that the time interval t2-t3 becomes unacceptably long, the control algorithm provides for an increase of the area A1 in a subsequent injection process so that the interval t2-t3 can be kept shorter. It is thus an adaptive control algorithm.

In the embodiment shown in FIG. 4, the pressure during the regulation interval t2-t3 is nearly constant. In an alternative thereto, the pressure during the regulation interval (corresponding to t2-t3) is decreased in several controlled steps and then drops to zero in a substantially linear end piece, similar to the piece A4 in FIG. 4. According to this embodiment, the time interval between two subsequent pressure reductions is variable and is determined by the control algorithm in such a way that the total area under the actual pressure curve corresponds to the desired nominal value. The pressure between two subsequent reductions is nearly constant, but may slightly decrease if there are any remaining leakages in the system. Such a decrease, however, is taken into account by the control mechanism as the actual pressure values are permanently measured. This alternative embodiment has the advantage that the passive pressure drop during the final interval (corresponding to t3-t4 in FIG. 4) is very small so that any nonlinearities in the pressure curve do not have a substantial effect on the injection accuracy. A further advantage is that the total injection time can be reduced.

It is understood that the controlled pressure increase from t0 to t1 and the controlled decrease from t1 to t2 need not necessarily be linear, but that other waveforms are possible, for example a somewhat curved pressure variation. Since the actual pressure is permanently measured, the integral under the pressure curve is always precisely known so that the injection can be performed with high accuracy.

Since the apparatus of the invention comprises a source of overpressure as well as a source of underpressure, the user has a high flexibility in influencing the liquid at hand. This is particularly useful in electrophoresis. After injection of the sample into the electrophoresis capillary, the pressure sources at the input end of the capillary can be used to move the entire liquid inside the capillary. By applying overpressure, the liquid column in the capillary can be moved in a forward direction, and by applying underpressure, it can be moved in a backward direction. If this procedure is applied during an electrophoretic separation, the length of the capillary is virtually increased so that the separation of the components can be improved. Furthermore, a component which has passed a detector at the output end of the capillary can be drawn back to detect it again. Generally, the user has a high flexibility in designing special procedures for his application by suitable combination of underpressure and overpressure. A further example is that the application of a defined positive pressure can be used for fraction collection.

An additional aspect of the apparatus of the invention is that it can also be used for a "negative" injection, i.e., an injection of sample into the output end of the capillary. Normally, the piece of the capillary in an electrophoresis apparatus between the location of the detector and the electrolyte vial at the output is not used for the actual separation and should be as short as possible. There are, however, applications wherein this short piece is used as a separation path for fast, qualitative measurements. For this purpose, the sample is to be injected into the output end of the capillary. The present invention can perform this task by applying a pressure-variation at the input end of the capillary which has the same schematic behaviour like the one shown in FIG. 4, but which is below zero, i.e., in the underpressure range. A further aspect of the invention arises if a mass spectrometer is coupled to the output of the electrophoresis capillary. In such a case, it cannot be completely avoided that an underpressure from the mass spectrometer acts on the capillary. In order to compensate this, a corresponding underpressure can be applied at the input end of the capillary by the source of underpressure.

We claim:

1. A method of injecting liquid into a capillary tube comprising the steps of immersing an end of the capillary tube in the liquid to be injected, applying a fluid pressure, different from ambient pressure, on the liquid to be injected, whereby liquid flows into the capillary tube, wherein, during an injection, the fluid pressure is continuously varied in a controlled way by correspondingly controlling a source of overpressure and a source of underpressure, with the fluid pressure increasing during a time interval t0-t1 and decreasing during another time interval t1-t2.

2. A method as in claim 1, wherein the time variation of the actual fluid pressure during an injection is measured, and wherein the fluid pressure provided by the source of overpressure or underpressure is controlled such that the time integral of the measured actual fluid pressure for an injection achieves a desired nominal value which is a measure of the amount of liquid to be injected into the capillary.

3. A method as in claim 2, wherein the time interval t0-t1 during which the fluid pressure increases and the time interval t1-t2 during which the fluid pressure decreases are determined by said nominal value, and wherein a variable time interval t2-t3 is provided the duration of which is determined by the actually measured pressure values during an injection to achieve said nominal value.

4. A method as in claim 3 wherein the fluid pressure during the variable time interval t2-t3 is substantially constant.

5. A method as in claim 3, wherein the time integral of the measured fluid pressure during the time interval t0-t1 when the pressure increases and during the time interval t1-t2 when the pressure decreases is substantially greater than the time integral of the measured fluid pressure for the rest of the injection period.

6. A method as in claim 4, wherein the time integral of the measured fluid pressure during the time interval t0-t1 when the pressure increases and during the time interval t1-t2 when the pressure decreases is substantially greater than the time integral of the measured fluid pressure for the rest of the injection period.

7. An apparatus for injecting liquid into a capillary tube by application of fluid pressure on the liquid comprising
means for immersing an end of the capillary (1) in the liquid,
a controllable source of overpressure,
a controllable source of underpressure,
means for applying the overpressure or the underpressure on the liquid, and—a controller for controlling the source of overpressure and the source of underpressure such that during an injection, the fluid pressure on the liquid continuously increases during a time interval t0-t1 and continuously decreases during another time interval t1-t2.

8. Apparatus as in claim 7, comprising a pressure sensor for measuring the time variation of the actual fluid pressure during an injection, with the output signal of the pressure sensor being supplied to the controller.

9. Apparatus as in claim 8, wherein the source of overpressure and the source of underpressure comprise a controllable valve, and a restrictor, respectively, and a working volume.

10. Apparatus as in claim 7, wherein the liquid to be injected is in a vial, and wherein lifting means are provided for lifting the vial towards an end of the capillary.

11. Apparatus as in claim 7, wherein the generation of overpressure and the generation of underpressure is performed by the same pump.

* * * * *